United States Patent
Miida et al.

(10) Patent No.: US 12,188,006 B2
(45) Date of Patent: Jan. 7, 2025

(54) METHOD FOR PRODUCING HIGHLY VIABLE DRIED MICROBIAL CELLS

(71) Applicant: KABUSHIKI KAISHA YAKULT HONSHA, Tokyo (JP)

(72) Inventors: Satoshi Miida, Tokyo (JP); Yuzuru Makino, Tokyo (JP); Akihisa Matsui, Tokyo (JP); Masahiko Ito, Tokyo (JP); Yasuhiro Moteki, Tokyo (JP)

(73) Assignee: KABUSHIKI KAISHA YAKULT HONSHA, Tokyo (JP)

( * ) Notice: Subject to any disclaimer, the term of this patent is extended or adjusted under 35 U.S.C. 154(b) by 744 days.

(21) Appl. No.: 17/041,749

(22) PCT Filed: Feb. 14, 2019

(86) PCT No.: PCT/JP2019/005204
§ 371 (c)(1),
(2) Date: Sep. 25, 2020

(87) PCT Pub. No.: WO2019/193841
PCT Pub. Date: Oct. 10, 2019

(65) Prior Publication Data
US 2021/0024878 A1    Jan. 28, 2021

(30) Foreign Application Priority Data
Apr. 5, 2018   (JP) .................................. 2018-072833

(51) Int. Cl.
*C12N 1/04*   (2006.01)
*C12N 1/20*   (2006.01)
*C12R 1/225*  (2006.01)

(52) U.S. Cl.
CPC .................. *C12N 1/04* (2013.01); *C12N 1/20* (2013.01); *C12N 1/205* (2021.05); *C12N 2523/00* (2013.01); *C12R 2001/225* (2021.05)

(58) Field of Classification Search
CPC . C12N 1/04; C12N 1/20; C12N 1/205; C12N 2523/00; C12R 2001/225
See application file for complete search history.

(56) References Cited

U.S. PATENT DOCUMENTS

| | | |
|---|---|---|
| 2012/0039853 A1 | 2/2012 | Corveleyn et al. |
| 2019/0062693 A1 | 2/2019 | Ito et al. |

FOREIGN PATENT DOCUMENTS

| | | | |
|---|---|---|---|
| JP | 3504365 B2 | 3/2004 | |
| JP | 2010-4787 A | 1/2010 | |
| JP | 2012-55288 A | 3/2012 | |
| JP | 2016-105705 A | 6/2016 | |
| WO | WO-2017073752 A1 * | 5/2017 | .......... A23L 33/135 |

OTHER PUBLICATIONS

Proom, H. and Hemmons, L.M. (1949) "The drying and preservation of bacterial cultures," Journal of General Microbiology, 3(1), pp. 7-18. Available at: https://doi.org/10.1099/00221287-3-1-7. (Year: 1949).*
Champagne, Claude P. et al. "Effect of Polymers and Storage Temperature on the Stability of Freeze-Dried Lactic Acid Bacteria." Food research international 29.5 (1996): 555-562. Web. (Year: 1996).*
Sullivan, M. L, and B. J Bradford. "Viable Cell Yield from Active Dry Yeast Products and Effects of Storage Temperature and Diluent on Yeast Cell Viability." Journal of dairy science 94.1 (2011): 526-531. Web. (Year: 2011).*
Machine translation of Ito et al. 2017, WO2017073752A1, published May 4, 2017, from Japanese to English by PE2E. (Year: 2023).*
Strasser S, Neureiter M, Geppl M, Braun R, Danner H. Influence of lyophilization, fluidized bed drying, addition of protectants, and storage on the viability of lactic acid bacteria. J Appl Microbiol. Jul. 2009; 107(1): 167-77. doi: 10.1111/j. 1365-2672.2009.04192.x. Epub Mar. 3, 2009. PMID: 19302330. (Year: 2009).*
Zhang J, Liu Q, Chen W, Du G, Chen J. Short communication: Protection of lyophilized milk starter Lactobacillus casei Zhang by glutathione. J Dairy Sci. Mar. 2016;99(3):1846-1852. doi: 10.3168/jds.2015-9540. Epub Dec. 24, 2015. PMID: 26723115. (Year: 2016).*
Dimitrellou, Dimitra, Panagiotis Kandylis, and Yiannis Kourkoutas. "Effect of Cooling Rate, Freeze-Drying, and Storage on Survival of Free and Immobilized Lactobacillus Casei ATCC 393." Food science & technology 69 (2016): 468-473. Web. (Year: 2016).*
The Extended European Search Report issued for the corresponding European Application No. 19780614.4 dated Nov. 23, 2021.
Anderson et al. "Storage Stability of Freeze-dried Starter Cultures (*Streptococcus thermophilus*) as Related to Physical State of Freezing Matrix", Lebensm, -Wiss,.u,-Technol, 32, pp. 540-547 (1999).
International Search Report issued in International Pat. Appl. No. PCT/JP2019/005204, 3504365dated May 14, 2019, along with an English translation thereof.
G.L. De Antoni et al. "Trehalose, a Cryoprotectant for Lactobacillus bulgaricus", Cryobiology 26, p. 149-153 (1989).

* cited by examiner

*Primary Examiner* — Louise W Humphrey
*Assistant Examiner* — John Paul Selwanes
(74) *Attorney, Agent, or Firm* — Greenblum & Bernstein, P.L.C.

(57) ABSTRACT

Provided is a novel technique for reducing damage and death of microbial cells through a method for producing highly viable dried microbial cells, the method being characterized by subjecting dried microbial cells to an alternating temperature treatment.

2 Claims, No Drawings

METHOD FOR PRODUCING HIGHLY VIABLE DRIED MICROBIAL CELLS

TECHNICAL FIELD

The present invention relates to a method for producing highly viable dried microbial cells having high viability after storage.

BACKGROUND ART

There exist many microorganisms having useful enzymatic activities and such microorganisms are widely utilized for the production of functional food materials such as carbohydrates, amino acids, and phospholipids.

In particular, among such microorganisms, lactic acid bacteria have been widely utilized conventionally for the production of dairy products such as yogurt and cheese, and in recent years, the development of foods, drinks, and the like using dried lactic acid bacteria has been advanced. Then, in order to obtain the effect of lactic acid bacteria, it is desired to utilize cells alive, but in the process of obtaining dried cells, the cells are often damaged and killed, and it was difficult to obtain a necessary amount of living cells.

As a technique for reducing damage and death of cells so far, for example, a technique for adjusting a dispersion medium to be used when drying cells is known (PTL 1, PTL 2, and NPL 1).

However, as a technique for reducing damage and death of cells, only a technique that is performed before the cells are dried has been known.

CITATION LIST

Patent Literature

PTL 1: Japanese Patent No. 3504365
PTL 2: JP-A-2010-4787

Non Patent Literature

NPL 1: G. L. DE ANTONI et al., "Trehalose, a Cryoprotectant for *Lactobacillus bulgaricus*", Cryobiology 26, pp. 149-153, 1989

SUMMARY OF INVENTION

Technical Problem

Accordingly, an object of the present invention is to provide a novel technique for reducing damage and death of cells.

Solution to Problem

The present inventors conducted intensive studies in order to achieve the above-mentioned object, and as a result, although heat stress generally causes a decrease in the viability of a microorganism, they surprisingly found that the viability after storage is improved by subjecting dried cells to an alternating temperature treatment corresponding to heat stress after the dried cells are obtained, and thus completed the present invention.

That is, the present invention is a method for producing highly viable dried microbial cells, characterized by subjecting dried microbial cells to an alternating temperature treatment.

Further, the present invention is a method for improving the viability of dried microbial cells, characterized by subjecting the dried microbial cells to an alternating temperature treatment.

Advantageous Effects of Invention

According to the present invention, the viability after storage of once produced dried microbial cells can be improved by a simple method of an alternating temperature treatment.

DESCRIPTION OF EMBODIMENTS

The method for producing highly viable dried microbial cells of the present invention (hereinafter referred to as "the production method of the present invention") is configured to subject dried microbial cells to an alternating temperature treatment.

The dried microbial cells to be used in the production method of the present invention are not particularly limited, however, examples thereof include cells obtained by drying microorganisms such as lactic acid bacteria. Examples of the lactic acid bacteria include *Lactobacillus* bacteria such as *Lactobacillus casei*, *Lactobacillus gasseri*, *Lactobacillus acidophilus*, *Lactobacillus cremoris*, *Lactobacillus helveticus*, *Lactobacillus salivarius*, *Lactobacillus fermentum*, *Lactobacillus yoghurti*, *Lactobacillus delbrueckii* subsp. *bulgaricus*, *Lactobacillus delbrueckii* subsp. *delbrueckii*, *Lactobacillus johnsonii*, and *Lactobacillus mali*, *Bifidobacterium* bacteria such as *Bifidobacterium bifidum*, *Bifidobacterium breve*, and *Bifidobacterium longum*, *Streptococcus* bacteria such as *Streptococcus thermophilus* and *Streptococcus lactis*, *Lactococcus* bacteria such as *Lactococcus lactis* subsp. *lactis*, *Lactococcus lactis* subsp. *cremoris*, *Lactococcusplantarum*, and *Lactococcus raffinolactis*, and *Enterococcus* bacteria such as *Enterococcus faecalis* and *Enterococcus faecium*. One species or two or more species of the lactic acid bacteria may be combined. Among the microorganisms, lactic acid bacteria are preferred. Among the lactic acid bacteria, lactic acid bacteria of the genus *Lactobacillus* are preferred, and *Lactobacillus casei* is more preferred, and *Lactobacillus casei* YIT 9029 (FERM BP-1366, date of deposit: May 1, 1981, the International Patent Organism Depositary, the National Institute of Technology and Evaluation (#120, 2-5-8 Kazusakamatari, Kisarazu-shi, Chiba-ken, 292-0818, Japan) is particularly preferred.

A method for obtaining dried cells by drying the microorganism is not particularly limited, and spray drying, lyophilization, or the like well known to those skilled in the art may be adopted. Specific examples of the method include methods described in Japanese Patent No. 3504365, JP-A-2010-4787, G. L. DE ANTONI et al., "Trehalose, a Cryoprotectant for *Lactobacillus bulgaricus*", Cryobiology 26, pp. 149-153, 1989, WO 2017/073752, and the like. Among these methods, the method described in WO 2017/073752 is preferred.

More specifically, the method described in WO 2017/073752 is performed as follows.

First, a microorganism is cultured according to a conventional method, and subsequently, the cells are collected according to a conventional method. Note that washing may be performed as needed between or before or after the culturing of the microorganism and the collection of the cells.

The thus collected microbial cells are added into a dispersion medium of an aqueous solution containing a protective agent, an antioxidant, and a chelating agent, preferably an aqueous solution composed of a protective agent, an antioxidant, and a chelating agent (hereinafter, also simply referred to as "dispersion medium") and suspended therein, and the resulting suspension is dried, whereby dried microbial cells are obtained.

Water to be used in the dispersion medium is not particularly limited, however, for example, drinkable water such as purified water or deionized water can be used.

The protective agent to be used in the dispersion medium is not particularly limited, however, for example, glutamic acid or a salt thereof such as sodium glutamate or potassium glutamate, a disaccharide such as trehalose, sucrose, lactose, or maltose, glycerol, maltodextrin, cyclodextrin, powdered skim milk, and the like are exemplified. Among the protective agents, it is preferred to use glutamic acid or a salt thereof and/or a disaccharide, and sodium glutamate and/or trehalose is more preferred. The content of the protective agent in the dispersion medium is not particularly limited, but is, for example, preferably 1 to 40 mass %, more preferably 5 to 30 mass %.

Further, the antioxidant to be used in the dispersion medium is not particularly limited, however, for example, ascorbic acid or a salt thereof such as sodium ascorbate or calcium ascorbate, vitamin E, catechin, glutathione, astaxanthin, or the like can be used, and among the antioxidants, sodium ascorbate is preferred. The content of the antioxidant in the dispersion medium is not particularly limited, but is, for example, preferably 0.01 to 10 mass %, more preferably 0.05 to 5 mass %.

Further, the chelating agent to be used in the dispersion medium is not particularly limited, however, for example, ethylenediaminetetraacetic acid (EDTA), citric acid or a salt thereof such as sodium citrate, phytic acid, or the like can be used. The content of the chelating agent in the dispersion medium is not particularly limited, but is, for example, preferably 0.1 to 10 mass %, more preferably 0.5 to 5 mass %.

As a preferred mode of the dispersion medium, an aqueous solution containing sodium glutamate, trehalose, sodium ascorbate, and sodium citrate is exemplified.

The amount of the microbial cells to be suspended in the dispersion medium is not particularly limited, however, for example, the microbial cell count in the suspension is about $1.0 \times 10^5$ to $4.0 \times 10^{14}$ cfu/mL, more preferably about $1.0 \times 10^7$ to $4.0 \times 10^{13}$ cfu/mL.

A method for drying the suspension is not particularly limited, and for example, a known drying method such as lyophilization or spray drying can be utilized, however, in order to increase the viability rate of a microorganism in the drying step, lyophilization is preferred. Examples of the drying conditions in the lyophilization method include conditions in which a freezing treatment at $-35°$ C. to $-45°$ C. for 6 to 12 hours is performed, and thereafter a drying treatment at $12°$ C. to $32°$ C. for 40 to 90 hours is performed.

The dried microbial cells obtained as described above are subsequently subjected to an alternating temperature treatment. Note that the dried microbial cells before the alternating temperature treatment are, for example, ground using a mill, and the ground cells are filled in capsules made of hydroxypropylmethylcellulose in an amount of 0.2 g per capsule under a general atmospheric composition without degassing, and then, the capsules are placed in a bag or the like made of aluminum or the like along with an oxygen absorber, and the dried microbial cells may be subjected to the alternating temperature treatment in such a state.

The alternating temperature treatment is a treatment in which a temperature load that is different from room temperature at which dried microbial cells are generally stored is applied for a given period or longer. Specifically, one or two or more treatments selected from the group consisting of the following (a) and (b) are performed:

(a) a treatment of heating to $30°$ C. or higher for 1 day or more; and (b) a treatment of cooling to $10°$ C. or lower for 1 day or more.

The treatments (a) and (b) can be performed singly or in combination or can be performed repeatedly.

Preferred examples of the treatment (a) include the following treatments:

(a1) a treatment of heating to $30°$ C. or higher, preferably 35 to $37°$ C. for 1 day or more, preferably 2 days; and (a2) a treatment of heating to $30°$ C. or higher, preferably 35 to $37°$ C. for 1 day or more, preferably 1 day.

Preferred examples of the treatment (b) include the following treatment:

(b1) a treatment of cooling to $10°$ C. or lower, preferably 2 to $10°$ C. for 1 day or more, preferably 1 day.

In a preferred alternating temperature treatment, for example, the treatment (a) is performed, or after performing the treatment (b), the treatment (a) is further performed, and in a more preferred alternating temperature treatment, the treatment (a1) is performed, or after performing the treatment (b1), the treatment (a1) is further performed or the treatment (a2) is further performed, and in a particularly preferred alternating temperature treatment, the treatment (a1) is performed.

Such an alternating temperature treatment can be performed by utilizing a device enabling heating such as a dryer or an autoclave in the case of heating, and can be performed by utilizing a device enabling cooling such as a refrigerator or a freezer in the case of cooling. Note that when performing such an alternating temperature treatment, pressure or the like is not particularly limited.

The thus obtained dried microbial cells have a viability of 110% or more as compared with the case where the dried microbial cells are not subjected to the alternating temperature treatment in the case of after 6-month storage, and have a viability of 120% or more, preferably a viability of 130 to 140% as compared with the case where the dried microbial cells are not subjected to the alternating temperature treatment in the case of after 12-month storage.

The highly viable dried microbial cells can be used for the same purpose as conventional dried microbial cells. Specifically, the highly viable dried microbial cells can be utilized in foods and drinks directly or by mixing with another food material to be generally added to foods. Examples of the foods include meat processed foods such as ham and sausages, processed fishery foods such as Kamaboko (boiled fish paste loaf) and Chikuwa (tube-shaped boiled fish paste cake), bread, confectionery, butter, and fermented milk such as yogurt. Further, examples of the drinks include soft drinks, dairy lactic acid bacteria drinks, and lactic acid bacteria drinks. In addition, examples of the forms of foods and drinks include generally used forms of foods and drinks, for example, a solid such as a powder and a granule, a paste, a liquid, and the like. Still further, the dried microbial cells may be formulated into, for example, a tablet, a powder, a chewable tablet, a hard capsule, a soft capsule, a pill, and the like.

EXAMPLES

Hereinafter, the present invention will be described in detail by showing Examples, however, the present invention is by no means limited to these Examples. Note that in the following Examples, the viable cell count of *Lactobacillus casei* was measured by the following method.

<Measurement Method for Viable Cell Count of *Lactobacillus Casei*

Dried cells of *Lactobacillus casei* were serially diluted with physiological saline (0.85 mass % sodium chloride). The diluted solution (1 mL) was mixed and diluted with a BCP plate count agar, and the cells were cultured at 37° C. for 72 hours. Thereafter, formed colonies were counted, and the obtained count was multiplied by the dilution ratio, and the obtained value was used as the viable cell count of *Lactobacillus casei*.

Example 1

Preparation of Dried Cells of *Lactobacillus Casei* and Alternating Temperature Treatment

*Lactobacillus casei* YIT 9029 was anaerobically cultured at 37° C. for 20 hours in a medium (pH 7) containing yeast extract (1 mass %), monopotassium phosphate (0.1 mass %), dipotassium phosphate (0.2 mass %), and lactose (2 mass %). After completion of culturing, the culture solution was cooled to a liquid temperature of 20° C. or lower, and the pH of the solution was adjusted to 7.0 with a 5 N sodium hydroxide solution. The cells obtained by centrifuging the culture solution (14000 G, 4° C., 30 minutes) were collected, and the cells were suspended at $2.0 \times 10^{11}$ cfu/mL in a dispersion medium prepared to a total volume of 1000 mL according to a composition containing sodium glutamate (10 mass %), trehalose (10 mass %), sodium ascorbate (1 mass %), and sodium citrate (1 mass %). The cell suspension was dispensed in a tray, and dried cells were prepared by a lyophilization method. Note that the lyophilization was performed using a lyophilizer (TAKARA FREEZE-DRYER TF20-80 TANNS, manufactured by TAKARA ATM Co., Ltd.) under the condition of shelf temperature of −40° C. for 9 hours, and thereafter, under the condition of shelf temperature of 20° C. for 80 hours. The obtained dried cells were ground using a mill, and the ground cells were filled in capsules (made of hydroxypropylmethylcellulose) in an amount of 0.2 g per capsule under a general atmospheric composition without degassing, and then, the capsules were placed in an aluminum pouch along with an oxygen absorber (manufactured by Mitsubishi Gas Chemical Company, Inc.).

The above-obtained aluminum pouch immediately after the production was heated at 35° C. for 2 days, and thereafter stored at 22° C. for 6 months (Implementation Method 1). Further, the above-obtained aluminum pouch immediately after the production was cooled at 2° C. for 1 day, and further heated at 35° C. for 2 days, and thereafter stored at 22° C. for 6 months (Implementation Method 2). Further, the above-obtained aluminum pouch immediately after the production was heated at 37° C. for 1 day, and thereafter stored at 22° C. for 6 months (Implementation Method 3). Note that the above-obtained aluminum pouch was stored at 22° C. for 6 months, and the resultant was used for comparison. The measurement results of the viable cell count before and after storage are shown in Table 1. Further, the viability rate was calculated from the viable cell counts using the following formula, and further, to what extent the respective Implementation Methods improved the viability as compared with the Comparative Method (no alternating temperature treatment) was calculated using the following formula. The results are also shown in Table 1.

TABLE 1

|  | Before storage | After 6-month storage | Viability rate | Improvement rate of viability |
|---|---|---|---|---|
| Comparative Method | $2730 \times 10^8$ cells/g | $618 \times 10^8$ cells/g | 22.6% | — |
| Implementation Method 1 | $2730 \times 10^8$ cells/g | $745 \times 10^8$ cells/g | 27.3% | 121% |
| Implementation Method 2 | $2730 \times 10^8$ cells/g | $700 \times 10^8$ cells/g | 25.6% | 113% |
| Implementation Method 3 | $2730 \times 10^8$ cells/g | $720 \times 10^8$ cells/g | 26.4% | 117% |

$$\text{Viability rate (\%)} = (\text{viable cell count after storage}/\text{viable cell count before storage}) \times 100 \quad [\text{Math. 1}]$$

$$\text{Improvement rate of viability (\%)} = (\text{viability rate of Implementation Method}/\text{viability rate of Comparative Method}) \times 100 \quad [\text{Math. 2}]$$

From the results, it was found that the viability rate after 6-month storage of each of the Implementation Methods is 25% or more, and therefore, each of the Implementation Methods provides at least a viability of 110% or more as compared with the case where the alternating temperature treatment was not performed (Comparative Method).

Example 2

Long-Term Storage of Dried Cells of *Lactobacillus Casei*

The dried cells after 6-month storage obtained in Example 1 were further stored at 22° C. for 6 months, and the measurement results of the viable cell count before and after storage measured in the same manner as in Example 1 are shown in Table 2. Further, the viability rate and the improvement rate of the viability were calculated in the same manner as in Example 1. The results are also shown in Table 2.

TABLE 2

|  | Before storage | After 12-month storage | Viability rate | Improvement rate of viability |
|---|---|---|---|---|
| Comparative Method | $2730 \times 10^8$ cells/g | $440 \times 10^8$ cells/g | 16.1% | — |
| Implementation Method 1 | $2730 \times 10^8$ cells/g | $590 \times 10^8$ cells/g | 21.6% | 134% |
| Implementation Method 2 | $2730 \times 10^8$ cells/g | $575 \times 10^8$ cells/g | 21.1% | 131% |
| Implementation Method 3 | $2730 \times 10^8$ cells/g | $580 \times 10^8$ cells/g | 21.2% | 132% |

From the results, it was found that the viability rate after 12-month storage of each of the Implementation Methods is 21% or more, and therefore, each of the Implementation Methods provides at least a viability of 130% or more as compared with the case where the alternating temperature treatment was not performed (Comparative Method).

INDUSTRIAL APPLICABILITY

The present invention can be utilized for the production of dried microbial cells.

The invention claimed is:

1. A method for improving viability of *Lactobacillus casei* cells dried by lyophilization, the method consisting of:
    heating the dried cells at 35 to 37° C. for 1 to 2 days prior to storage; or
    cooling the dried cells at 2° C. for 1 day, and then heating the dried cells at 35 to 37° C. for 1 to 2 days prior to storage,
    wherein the storage is at 22° C. or lower.

2. The method according to claim 1, wherein the *Lactobacillus casei* cells are *Lactobacillus casei* YIT 9029 cells.

\* \* \* \* \*